United States Patent
Bryant

(10) Patent No.: US 10,004,184 B2
(45) Date of Patent: Jun. 26, 2018

(54) APPARATUS AND METHOD FOR THREE-DIMENSIONAL MOISTURE CONTROL USING SPRINKLERS

(71) Applicant: Bryant Consultants, Inc., Carrollton, TX (US)

(72) Inventor: John Bryant, Carrollton, TX (US)

(73) Assignee: BRYANT CONSULTANTS, INC., Carrollton, TX (US)

( * ) Notice: Subject to any disclaimer, the term of this patent is extended or adjusted under 35 U.S.C. 154(b) by 309 days.

(21) Appl. No.: 14/728,330

(22) Filed: Jun. 2, 2015

(65) Prior Publication Data

US 2016/0353679 A1 Dec. 8, 2016

(51) Int. Cl.
*A01G 25/16* (2006.01)
*G05B 19/042* (2006.01)
*G01N 27/04* (2006.01)

(52) U.S. Cl.
CPC ......... *A01G 25/167* (2013.01); *G05B 19/042* (2013.01); *G01N 27/048* (2013.01); *G05B 2219/2625* (2013.01)

(58) Field of Classification Search
None
See application file for complete search history.

(56) References Cited

U.S. PATENT DOCUMENTS

| | | |
|---|---|---|
| 5,341,831 A | 8/1994 | Zur |
| 5,537,045 A | 7/1996 | Henderson |
| 5,621,669 A * | 4/1997 | Bjornsson ............ A01G 25/167 239/63 |
| 5,847,568 A | 12/1998 | Stashkiw et al. |
| 5,914,603 A | 6/1999 | Daily et al. |
| 5,927,603 A | 7/1999 | McNabb |
| 6,060,889 A | 5/2000 | Hooker |
| 6,147,497 A | 11/2000 | Berryman et al. |

(Continued)

OTHER PUBLICATIONS

'Landscape Watering by the Numbers' by DiFrancesco and Baker, 2003.*

(Continued)

*Primary Examiner* — Mohammad Ali
*Assistant Examiner* — Bernard G Lindsay
(74) *Attorney, Agent, or Firm* — Schultz & Associates, P.C.

(57) ABSTRACT

A system and method for moisture control includes a computer, a probe controller connected to the computer, a set of probes connected to the probe controller, a sprinkler controller connected to the computer, and a set of sprinklers connected to the sprinkler controller. The set of probes are driven into the ground according to a predetermined set of positions. A set of high voltage currents is injected into the ground through the set of probes and measurements are taken. A three-dimensional resistivity model is generated from the measurements and is compared to a set of moisture requirements. A set of sprinkler commands is generated based on the three-dimensional resistivity model and the set of moisture requirements. If the three-dimensional resistivity model meets the set of moisture requirements, the set of sprinklers are activated in each of a set of sprinkler zones according the three-dimensional resistivity model where watering is needed.

4 Claims, 13 Drawing Sheets

(56) References Cited

U.S. PATENT DOCUMENTS

| | | |
|---|---|---|
| 6,281,801 B1 | 8/2001 | Cherry et al. |
| 6,295,512 B1 | 9/2001 | Bryant |
| 6,331,778 B1 | 12/2001 | Daily et al. |
| 6,618,673 B2 | 9/2003 | Zur |
| 6,663,012 B2 | 12/2003 | Condreva |
| 6,978,794 B2 | 12/2005 | Dukes et al. |
| 7,063,271 B2 | 6/2006 | Lashgari |
| 7,261,245 B2 | 8/2007 | Zur |
| 7,810,515 B2 | 10/2010 | Nies et al. |
| 8,104,498 B2 | 1/2012 | Dresselhaus et al. |
| 8,598,882 B2 | 12/2013 | Meekes |
| 8,671,969 B2 | 3/2014 | Dresselhaus et al. |
| 2006/0108439 A1* | 5/2006 | Zur .................... A01G 25/167 239/63 |
| 2006/0204647 A1 | 9/2006 | Calabrese |
| 2010/0012744 A1* | 1/2010 | Kates .................... A01G 25/167 239/11 |
| 2011/0043230 A1 | 2/2011 | Morton |
| 2013/0226347 A1 | 8/2013 | Martinez |
| 2014/0371928 A1* | 12/2014 | Ersavas .................... A01G 1/00 700/284 |

OTHER PUBLICATIONS

Fliwer, "Plant & Play", Inolve USA, http://fliwer.com/ (undated).

Gardena, "Soil Moisture Sensor", http://www.gardena.com/int/water-management/water-controls/soil-moisture-sensor, (undated).

Kelly, et al., "Better Placement of Soil Moisture Point Measurements Guided by 2D Resistitve Tomography for Improved Irrigation Scheduling", Soil Research, Aug. 25, 2011, vol. 49(6), CSIRO Publishing.

OSO Simple Technologies, Inc. "Plant Link", http://myplantlink.com/, (undated).

Rain Bird, "Flow Sensors and Transmitters", http://www.rainbird.com/landscape/products/central/flowsensors.htm, (undated).

UGMO, "The UG1000 Soil Moisture Sensor System", www.ugmo.com/products/ug1000, (undated), King of Prussia, Pennsylvania.

* cited by examiner

APPARATUS AND METHOD FOR THREE-DIMENSIONAL MOISTURE CONTROL USING SPRINKLERS

FIELD OF THE INVENTION

The present invention relates to computer controlled sprinkler systems. In particular, the present invention relates to an apparatus and method for three-dimensional moisture control.

BACKGROUND OF THE INVENTION

Many different entities consume fresh water resources including farming, municipalities for drinking water, industrial companies, and residences. As population and urbanization increases, the demand from these entities on fresh water resources further increases, thereby making conservation and efficient use of fresh water critical. One common problem is the frequent over use of water. For example, sprinkler systems running during or immediately after rain or during freezing temperatures, resulting in the waste of large quantities of water and dangerous conditions due to ice formation.

Recently, agricultural and residential uses of water have become the focus of conservation and efficiency efforts. For example, local municipalities have implemented watering restrictions and in some places entire watering bans. Various types of equipment have been developed to limit watering, including automatic timers, rain sensors, and freeze sensors, which control an entire sprinkler system. However, a typical residential yard includes grass, shrubs, and trees, each of which requires different watering amounts to remain healthy. These solutions do not account for these different levels of watering needs, leading to the death of plants and soil erosion, which contaminates water supplies only making such resources more scarce.

The prior art has attempted to solve these problems with limited success. For example, U.S. Pat. No. 6,978,794 to Dukes discloses an automatic control system and method for irrigation. The system includes a control device connected to an irrigation structure to control the water flow. A set of time domain reflectometry sensors is connected to the control device to measure moisture in the soil. The control device determines whether to irrigate the soil based on the measurements received from the set of time domain reflectometry sensors. If needed, the control device activates the irrigation structure to irrigate the soil. However, the system in Dukes requires the time domain reflectometry sensors to be buried at different depths in order to measure moisture, thereby leading to inaccurate measurements. Further, the system in Dukes cannot generate a three dimensional resistivity model.

U.S. Pat. No. 7,063,271 to Lashgari discloses a moisture responsive sprinkler circuit. The sprinkler circuit includes a control circuit and a moisture responsive circuit. The control circuit is connected between a sprinkler controller (e.g., timer) and a sprinkler valve, and is powered by a valve signal sent from the sprinkler controller to the valve. The moisture responsive circuit includes two pairs of electrodes wired in series and residing at different depths. When resistance across both pairs of electrodes drops sufficiently, a relay in the control circuit opens and interrupts the valve signal to the valve to control irrigation. However, the pair of electrodes must be placed at different depths that depend on the root depth of a plant in order to work properly resulting in time consuming installation. Further, because the root depth changes as the plant grows, the electrodes are easily misaligned with the root depth leading to inaccurate measurements.

U.S. Pat. No. 8,671,969 to Dresselhaus discloses a moisture sensor buried in the soil that measures a moisture level of the surrounding soil. Each watering zone within an irrigation system has a moisture sensor buried in the soil to individually monitor and determine how much water is needed in each zone. The moisture sensor includes control functionality and acts as a regulator for the watering zone in which the moisture sensor is located. The moisture sensor regulates the amount of water the zone receives by preventing actuation of a solenoid valve based upon a moisture level reading. The moisture sensor is coupled between an irrigation controller and the solenoid valve. Once supplied power from the irrigation controller, the moisture sensor supplies power to the solenoid valve so long as the moisture level of the soil is not above a threshold level. The power to the solenoid valve actuates the solenoid valve and allows water to flow to sprinklers. However, the sensor in Dresselhaus does not account for different vegetation within each zone and thereby can still lead to overwatering or underwatering within each zone.

Therefore, there is a need in the art for a system that measures soil moisture at different depths in three dimensions. There is a further need for a system and method for controlling a sprinkler system based on plant moisture requirements. There is still a further need for a system and method for controlling a sprinkler system based on a three-dimensional moisture model.

SUMMARY

A system and method for moisture control is disclosed. The system includes a computer, a probe controller connected to the computer, a set of probes connected to the probe controller, a sprinkler controller connected to the computer, and a set of sprinklers connected to the sprinkler controller. The set of probes are driven into the ground according to a predetermined set of positions.

According to a control process saved in and executed by the computer, the probe controller injects a set of high voltage currents into the ground through the set of probes and measures a voltage across the set of probes to create a set of probe data. The computer receives a set of moisture requirements and the set of probe data. A three-dimensional resistivity model is generated from the set of probe data and is compared to the set of moisture requirements. A set of sprinkler commands is generated based on the three-dimensional resistivity model and the set of moisture requirements.

If the three-dimensional resistivity model meets the set of moisture requirements, the set of sprinklers are activated in each of a set of sprinkler zones according the three-dimensional resistivity model where watering is needed.

BRIEF DESCRIPTION OF THE DRAWINGS

In the detailed description presented below, reference is made to the accompanying drawings.

DETAILED DESCRIPTION

It will be appreciated by those skilled in the art that aspects of the present disclosure may be illustrated and described in any of a number of patentable classes or contexts including any new and useful process or machine or any new and useful improvement. Aspects of the present disclosure may be implemented entirely in hardware, entirely in software (including firmware, resident software, micro-code, etc.) or combining software and hardware implementation that may all generally be referred to herein as a "circuit," "module," "component," or "system." Further, aspects of the present disclosure may take the form of a computer program product embodied in one or more computer readable media having computer readable program code embodied thereon.

Figure 1:
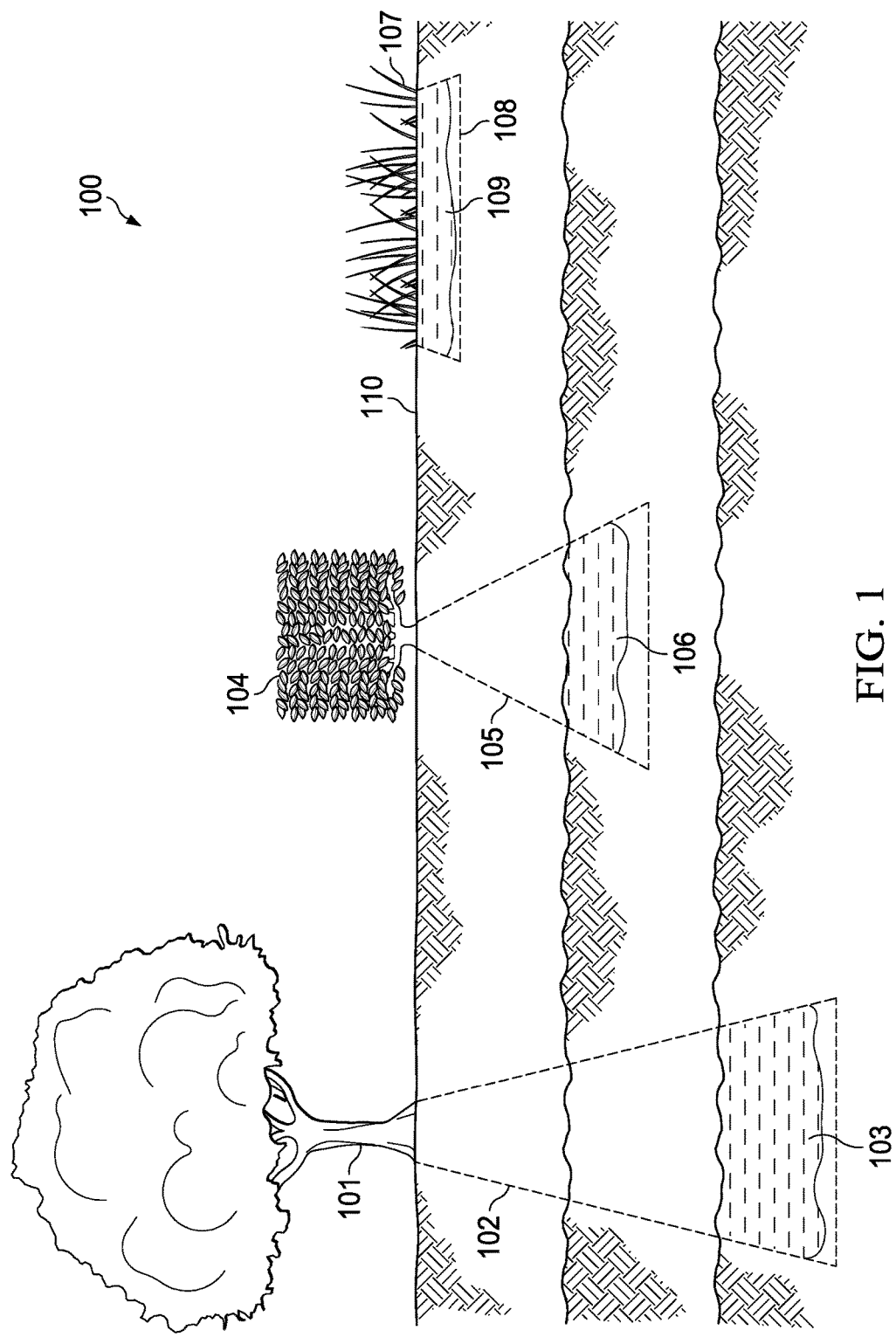
FIG. 1 is a schematic of water depths for different types of foliage.

Referring to FIG. 1, different foliage requires different amounts of water at different depths. For example, tree 101 has root system 102. Root system 102 has watering depth 103. Bush 104 has root system 105. Root system 105 has watering depth 106. Grass 106 has watering depth 107. It can be seen that tree 101, bush 104 and grass 107 all require water at different depths below ground level 110.

Figure 2:
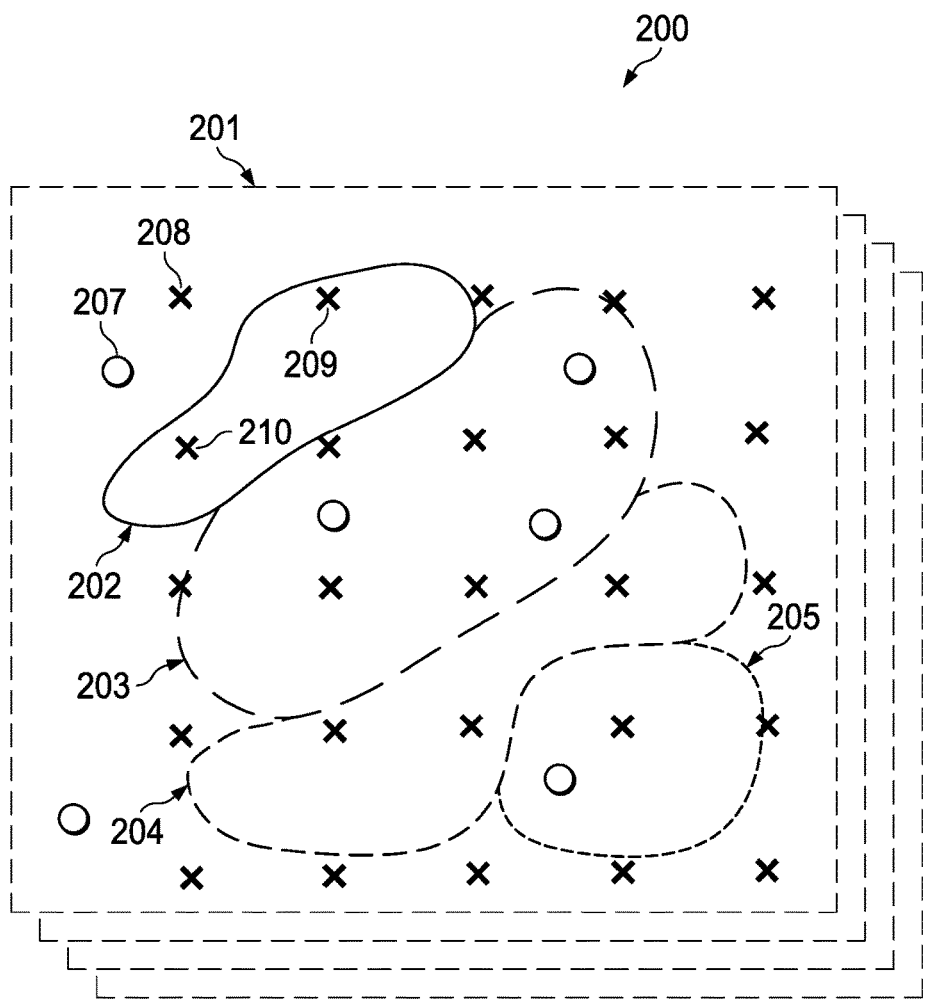
FIG. 2 is a schematic of various soil types and sprinkler locations.

Referring to FIG. 2, various soil types and odd sprinkler locations can at different locations require that different watering amounts occur at different times in order to assure a uniform moisture level. Watering zone 201 includes soil types 202, 203, 204, and 205, each of which is a different type of soil that absorbs water at a different rate. Different soil types can overlap and assume irregular patterns. Watering zone 201 further includes a set of sprinklers 207. The placement of the set of sprinklers 207 are denoted in the drawing by "0"s. As can be seen, the placement of the set of sprinklers 207 are often irregular and do not match soil types 202, 203, 204, and 205 or placement of foliage.

In a preferred embodiment, a set of probes 206 is placed at a regular interval to generate a three-dimensional resistivity map. The set of probes 206 are denoted in the drawing as "X"s. As will be further described below, the three-dimensional resistivity map is used to determine a watering schedule for watering zone 201 to assure a uniform moisture level.

In a preferred embodiment, the set of probes 206 is placed in a grid-like pattern. In other embodiments, other patterns may be employed.

In a preferred embodiment, each of the set of probes 206 is located in a range from approximately three (3) feet to approximately thirty (30) from each other. Other intervals may be employed.

In a preferred embodiment, each probe has a set of location coordinates. For example, Cartesian coordinates are employed. Probe 208 has the coordinates (0,0), probe 209 has the coordinates (0,1), and probe 210 has the coordinates (1,0). The remaining probes have coordinates that follow in the described manner. Other coordinate systems may be employed.

Figure 3:
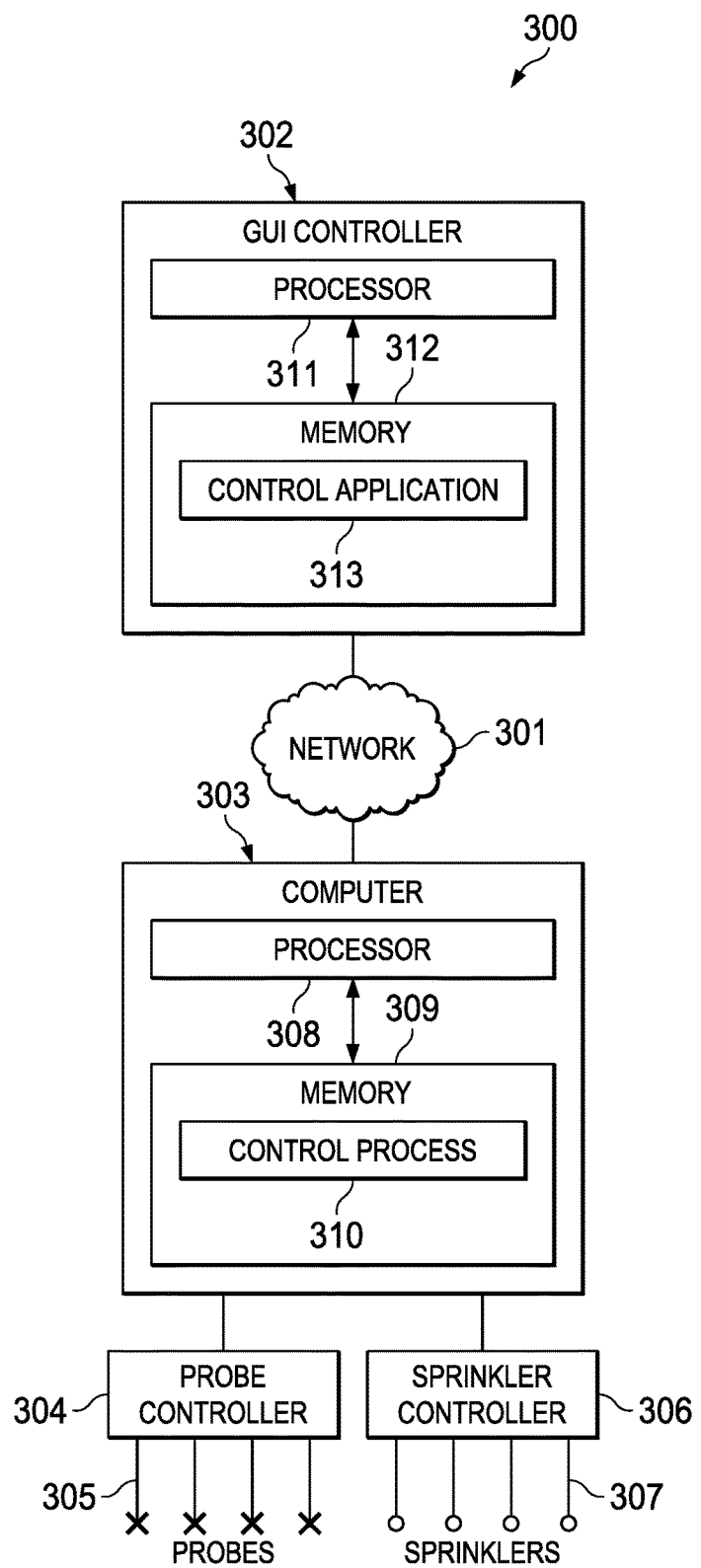
FIG. 3 is a schematic of a system for controlling sprinklers using a three-dimensional resistivity model of a preferred embodiment.

Referring to FIG. 3, system 300 includes network 301, graphic user interface ("GUI") controller 302 connected to network 301, and computer 303 connected to network 301. Probe controller 304 is connected to computer 303 and to a set of probes 305. Sprinkler controller 306 is connected to computer 303 and a set of sprinklers 307. Computer 303 includes processor 308 and memory 309 connected to processor 308. Control process 310 is stored in memory 309 and executed by processor 308.

GUI controller 302 includes processor 311 and memory 312 connected to processor 311. In one embodiment, control application 313 is stored in memory 312 and executed by processor 311. In this embodiment, control application 313 is a native application, such as a mobile application, and interfaces with and controls control process 310 through network 301. In another embodiment, control application 313 is a web application stored on a third party server.

In a preferred embodiment, control process 310 utilizes probe controller 304 and the set of probes 305 to produce a set of electrical resistivity tomography models, as will be further described below. Electrical resistivity tomography applies a known current to alternating pairs of electrodes i.e., the set of probes, and then measuring electrical potential across other alternating pairs of electrodes. The measurements allow calibration of electrical resistivity (or conductance) over a plurality of vertical planes in soil. Differences in the resistivity correlate directly to migration of ground moisture. The set of electrical resistivity tomography models is used to generate a three-dimensional resistivity model.

In one embodiment, network 301 is a wide area network such as the internet. In another embodiment, network 301 is a local area network. In another embodiment, network 301 is a combination of a wide area network connected to a local area network.

In one embodiment, GUI controller 302 is a laptop computer. In another embodiment, GUI controller 302 is a smart phone. In another embodiment, GUI controller 302 is a tablet computer. Any computing device known in the art may be employed.

In a preferred embodiment, sprinkler controller 306 is any multi-zone programmable sprinkler controller known in the art.

Figure 4:
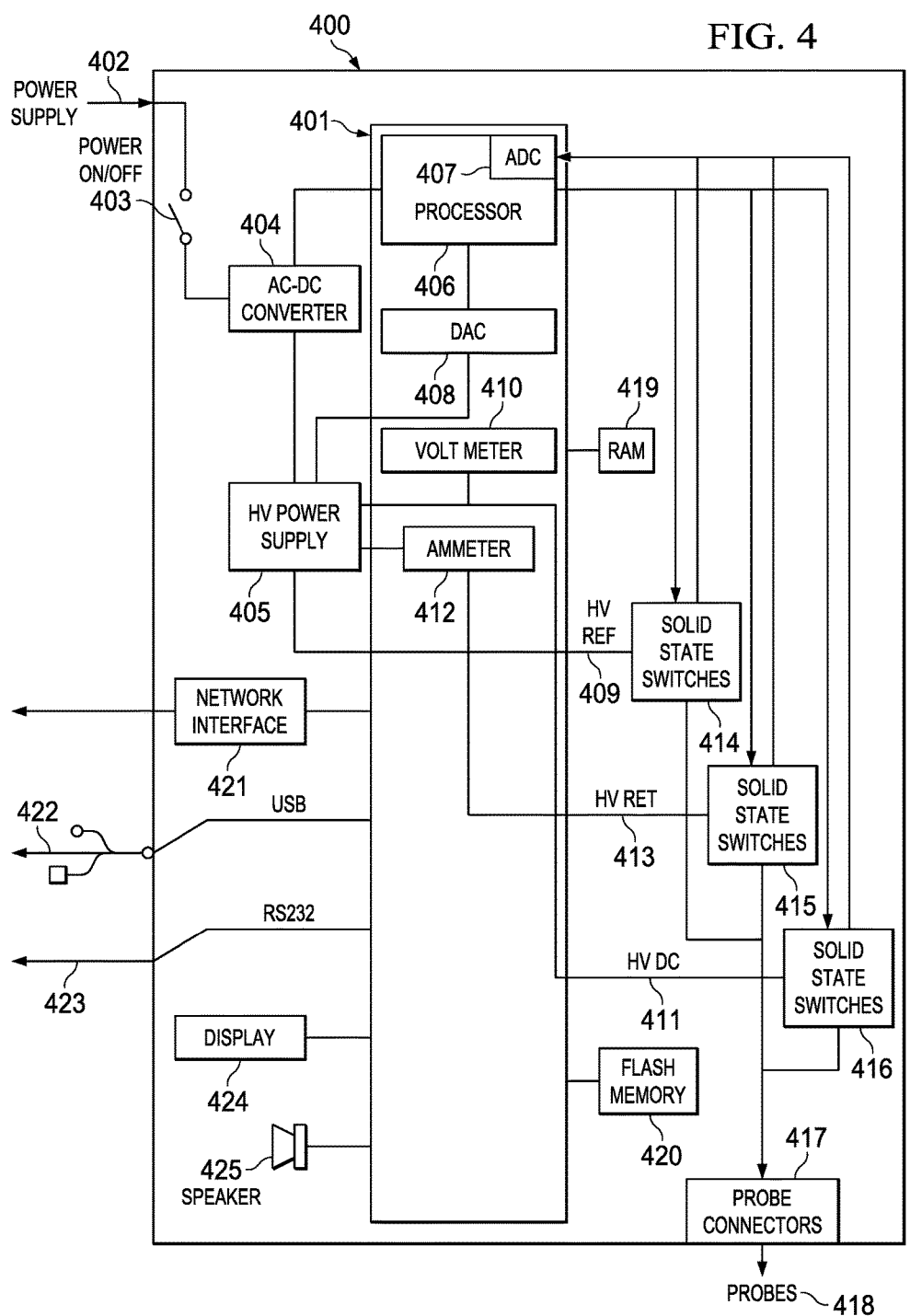
FIG. 4 is a schematic of a probe controller of a preferred embodiment.

Referring to FIG. 4, probe controller 304 will be further described as probe controller 400. Probe controller 400 is a power distribution unit containing power distribution electronics 401 for carrying out the logic functions for probe controller 400. Power supply 402 is connected to probe controller 400 through switch 403. Switch 403 is connected to AC-DC converter 404, which is connected to high voltage power supply 405 and to processor 406. Analog-to-digital converter ("ADC") 407 is connected to and read by processor 406. Digital-to-analog converter ("DAC") 408 is connected to processor 406 and to high voltage power supply 405. High voltage power supply 405 is connected to high voltage reference line 409. Volt meter 410 is connected to high voltage direct current line 411 and to processor 406 for measuring voltage. Processor 406 measures the output voltage of high voltage direct current line 411 with volt meter 409. Ammeter 412 is connected between high voltage power supply 405 and high voltage return line 413. Ammeter 410 is further connected to and read by processor 406 for measuring current.

High voltage reference line 409 is connected to a set of solid state switches 414. Set of solid state switches 414 is connected to processor 406 and to probe connectors 417. High voltage return line 413 is connected to set of solid state switches 415. Set of solid state switches 415 is connected to processor 406 and to probe connectors 417. High voltage direct current line 411 is connected to set of solid state switches 416. Set of solid state switches 416 is connected to processor 406 and to set of probe connectors 417. A set of probes 418 is connected to set of probe connectors 417.

Each of RAM 419 and flash memory 420 is connected to processor 406. Each of network interface 421, USB port 422, RS232 port 423, display 424, and speaker 425 is connected to processor 406.

In the preferred embodiment, high voltage power supply 405 is a 1C24-P250 from UltraVolt, Inc. with a maximum output voltage of 800V and a current limit of 2 A. Other suitable high voltage power supplies known in the art may be employed.

In a preferred embodiment, processor 406 is model MSP430 from Texas Instruments. In this embodiment, ADC 407 is integrated into processor 406. Other suitable processors and ADCs known in the art may be employed.

In a preferred embodiment, each of solid state switches 414, 415, and 416 is a solid state relay part no. GDH12028ZD3 from Greego Electric Co. Ltd. Other suitable solid state switches known in the art may be employed.

In a preferred embodiment, set of probe connectors 417 is a PT/26482 Series I insert-receptacle arrangement from Amphenol Industrial Products Group. Other suitable connectors known in the art may be employed.

In use, probe controller 400 switchably controls a set of output power lines, high voltage reference line 409, high voltage return line 413, and high voltage direct current line 411, for providing high voltage current to the set of probes 418.

Processor 406 controls high voltage power supply 405 to send a voltage between zero and the maximum output of high voltage power supply 405 to high voltage direct current line 411. Processor 406 measures the output voltage of high voltage power supply 405, for proportional control of high voltage direct current line 411. Ammeter 412 measures the current being delivered to the set of probes 418. The voltage and current measurements are sent to a connected computer via network interface 421, USB port 422, or RS232 port 423.

In a preferred embodiment, each probe of the set of probes 418 is simultaneously connected to probe connectors 417.

In a preferred embodiment, the set of probes 418 includes a reference probe and a subset of measurement probes. In this embodiment, probe controller 400 selectively connects and disconnects to the reference probe and the subset of measurement probes, impresses a known current, and measures the voltage across the reference probe and the subset of measurement probes, as will be further described below.

In a preferred embodiment, processor 406 controls sets of solid state switches 414, 415, and 416 to connect and disconnect high voltage signals to and from the reference probe and the subset of measurement probes according to a control process. Set of solid state switches 414 opens and closes a path between high voltage reference line 409 and the reference probe. Set of solid state switches 415 opens and closes a current path between high voltage return line 413 and the subset of measurement probes. Set of solid state switches 416 opens and closes a current path between high voltage direct current line 411 and the subset of measurement probes.

Figure 5:
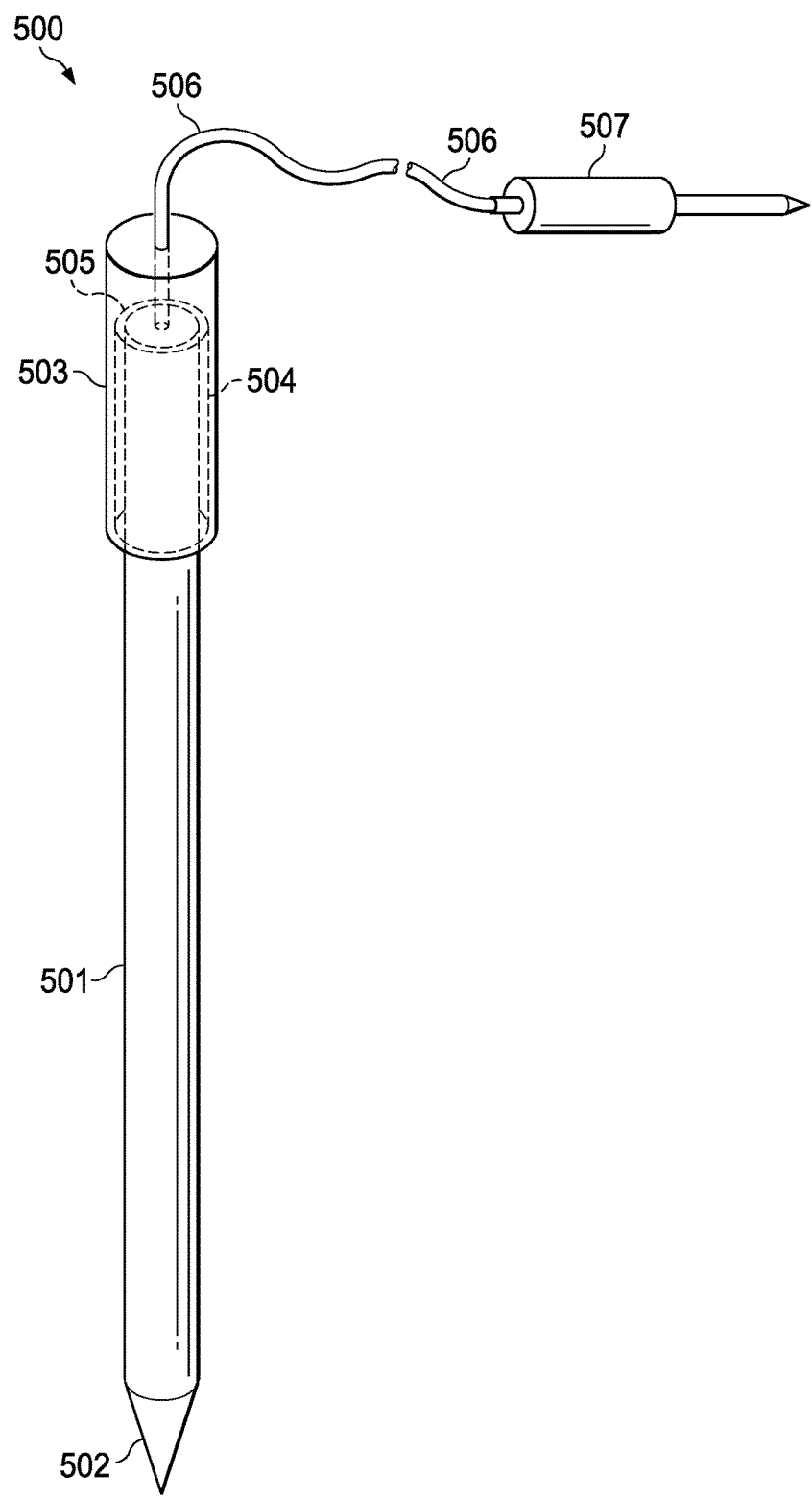
FIG. 5 is a side view of a probe of a preferred embodiment.

Referring to FIG. 5, probe 500 includes shaft 501 and tip 502 integrally formed on shaft 501. Cap 503 includes recess 504 to frictionally receive shaft 501. Cap 503 is sealed onto the shaft with a suitable adhesive. Cap 503 further includes contact 505. Contact 505 is connected to cable 506. Cable 506 is connected to connector 507.

In a preferred embodiment, shaft 501 and tip 502 are made of steel. Other suitable conductive materials may be employed.

In a preferred embodiment, cap 503 is made of polyvinylchloride. Other insulating materials, such as rubber, rubber-like polymers and plastics, may be employed.

In a preferred embodiment, contact 505 is a copper disk. In other embodiments, other suitable conductive materials, such as platinum, are employed.

In a preferred embodiment, cable 506 is an insulated copper cable. Other suitable insulated cables may be employed.

In a preferred embodiment, connector 507 is a PT/26482 Series I insert-receptacle arrangement from Amphenol Industrial Products Group. Other suitable connectors known in the art may be employed.

Referring to FIGS. 6A, 6B, 6C, 6D, 6E, and 6F, a schematic of a method for obtaining a resistivity model will be further described. In order to create a complete resistivity model, a voltage must be measured at every possible permutation of probes in an array. Moreover, in order to obtain a complete resistivity model, a current source must also be connected to every possible permutation of probes.

Figure 6A:
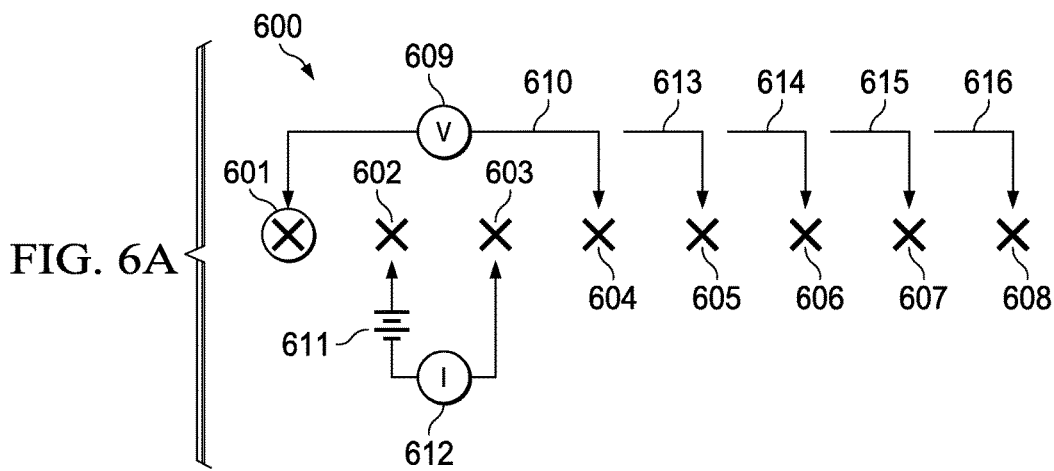
FIG. 6A is a schematic of a series of permutations of the locations of an ammeter and a current source and a volt meter of a preferred embodiment.

Referring to FIG. 6A, volt meter 609 is connected to reference probe 601 and to probe 604 of array 600 at connection 610. Ammeter 612 and current source 611 are connected to probes 602 and 603. A measured current is injected into the ground through probes 602 and 603. Voltage is measured across reference probe 601 and probe 604. While volt meter 609 remains connected to reference probe 601, volt meter 609 is further sequentially connected to probes 605, 606, 607, and 608 at connections 613, 614, 615, and 616, respectively. A measured current is injected and a voltage measurement is taken at each connection.

Figure 6B:
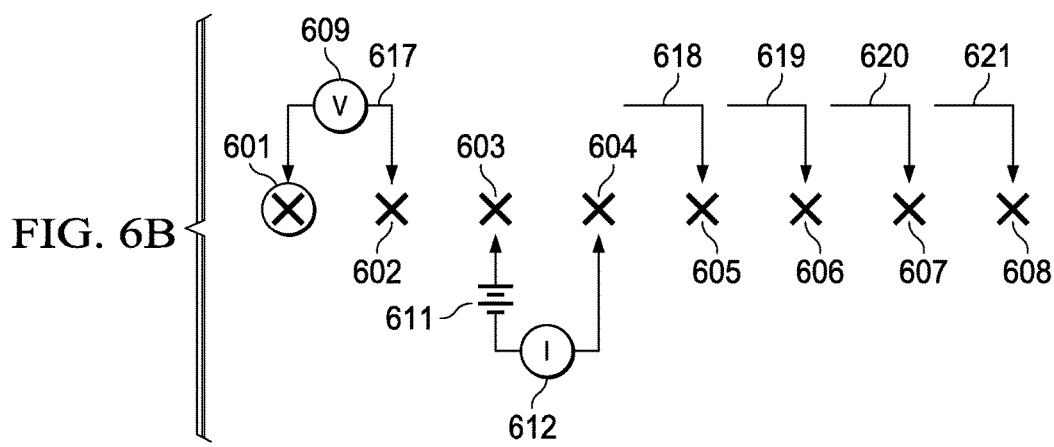
FIG. 6B is a schematic of a series of permutations of the locations of an ammeter and a current source and a volt meter of a preferred embodiment.

Referring to FIG. 6B, ammeter 612 and current source 611 are connected to probes 603 and 604. Volt meter 609 is connected to reference probe 601 and probe 602 at connection 617. A measured current is injected into the ground through probes 603 and 604. Voltage across reference probe 601 and probe 602 is measured. Volt meter 609 is then sequentially connected to reference probe 601 and probes 605, 606, 607, and 608 at connections 618, 619, 620, and 621, respectively. A measured current is injected and a voltage measurement is taken at each connection of volt meter 609.

Figure 6C:
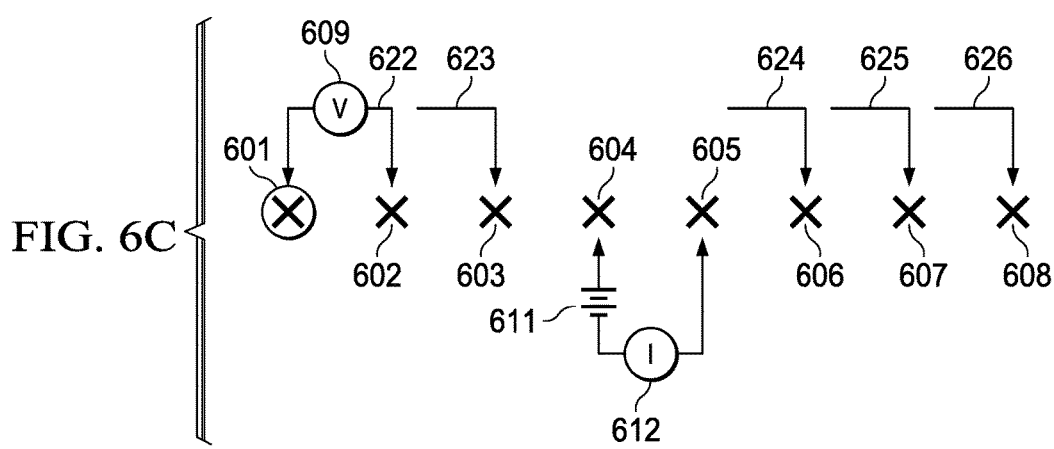
FIG. 6C is a schematic of a series of permutations of the locations of an ammeter and a current source and a volt meter of a preferred embodiment.

Referring to FIG. 6C, ammeter 612 and current source 611 are connected to probes 604 and 605. Volt meter 609 is connected to reference probe 601 and probe 602 at connection 622. A measured current is injected into the ground through probes 604 and 605. Voltage across reference probe 601 and probe 602 is measured. Volt meter 609 is then sequentially connected to reference probe 601 and probes 603, 606, 607, and 608 at connections 623, 624, 625, and 626, respectively. A measured current is injected and a voltage measurement is taken at each connection of volt meter 609.

Figure 6D:
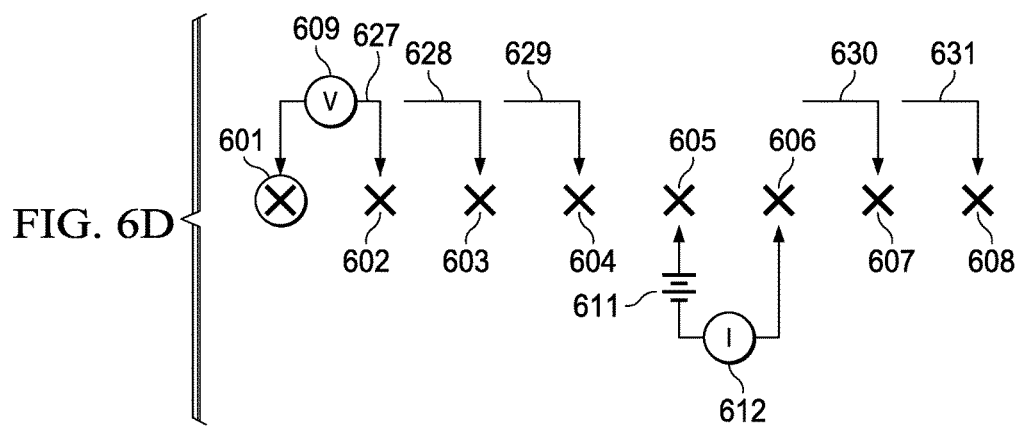
FIG. 6D is a schematic of a series of permutations of the locations of an ammeter and a current source and a volt meter of a preferred embodiment.

Referring to FIG. 6D, ammeter 612 and current source 611 are connected to probes 605 and 606. Volt meter 609 is connected to reference probe 601 and probe 602 at connection 627. A measured current is injected into the ground through probes 605 and 606. Voltage across reference probe 601 and probe 602 is measured. Volt meter 609 is then sequentially connected to reference probe 601 and probes 603, 604, 607, and 608 at connections 628, 629, 630, and 631, respectively. A measured current is injected and a voltage measurement is taken at each connection of volt meter 609.

Figure 6E:
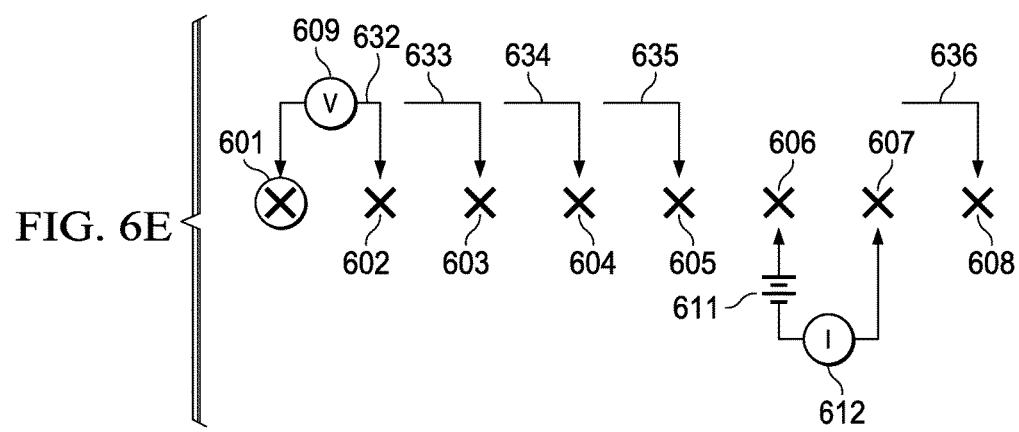
FIG. 6E is a schematic of a series of permutations of the locations of an ammeter and a current source and a volt meter of a preferred embodiment.

Referring to FIG. 6E, ammeter 612 and current source 611 are connected to probes 606 and 607. Volt meter 609 is connected to reference probe 601 and probe 602 at connection 632. A measured current is injected into the ground through probes 601 and 602. Voltage across reference probe 601 and probe 602 is measured. Volt meter 609 is then sequentially connected to reference probe 601 and probes 603, 604, 605, and 608 at positions 633, 634, 635, and 636, respectively. A measured current is injected and a voltage measurement is taken at each connection of volt meter 609.

Figure 6F:
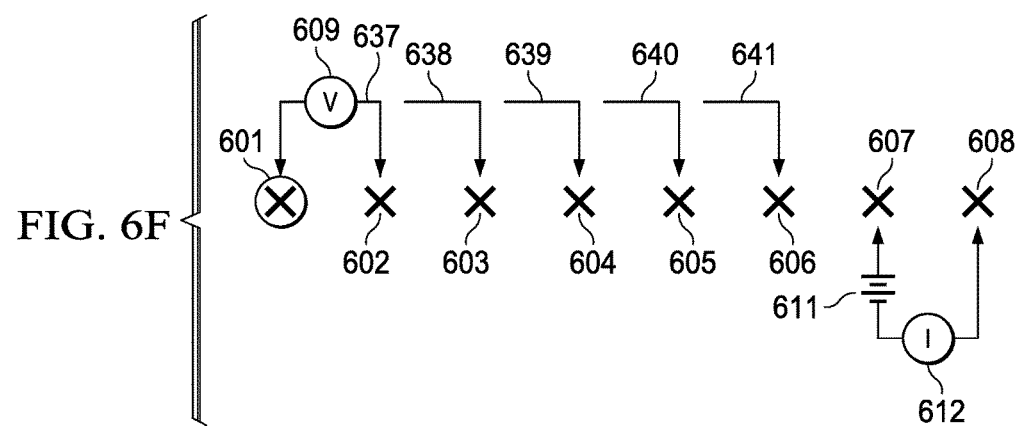
FIG. 6F is a schematic of a series of permutations of the locations of an ammeter and a current source and a volt meter of a preferred embodiment.

Referring to FIG. 6F, ammeter 612 and current source 611 are connected to probes 607 and 608. Volt meter 609 is connected to reference probe 601 and probe 602 at connection 637. A measured current is injected into the ground through probes 601 and 602. Voltage across reference probe 601 and probe 602 is measured. Volt meter 609 is then sequentially connected to reference probe 601 and probes 603, 604, 605, and 606 at connections 638, 639, 640, and 641, respectively. A measured current is injected and a voltage measurement is taken at each connection of volt meter 609.

In a preferred embodiment, the method described in FIGS. 6A, 6B, 6C, 6D, 6E, and 6F is repeated for each of a set of arrays.

Other permutations of connections for injecting current and taking measurements between an array of electrodes are envisioned by the preferred embodiment. Those skilled in the art will recognize that the current can be injected at many different locations in a given array, not only those shown in FIGS. 6A, 6B, 6C, 6D. 6E, and 6F. All possible permutations are also envisioned as embodiments of this preferred embodiment.

Figure 7:
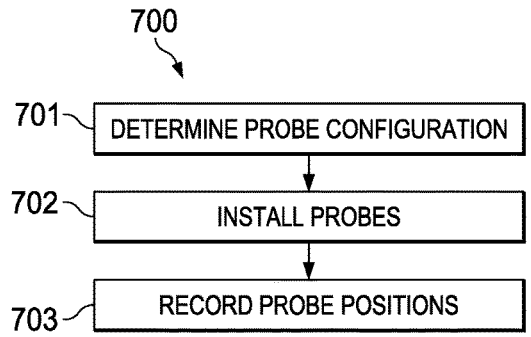
FIG. 7 is a flowchart of a setup process of a preferred embodiment.

Referring to FIG. 7, setup method 700 will be further described. At step 701, a configuration and a position for each of the set of probes is determined. For example, the set of probes are configured in a grid-like configuration. Once the configuration is determined a position for each probe in the configuration is determined. For example, in the grid configuration the positions are determined based on Cartesian coordinates.

At step 702, each of the set of probes is installed by driving each probe into the ground at its determined position and connecting each probe to the probe controller. At step 703, the position of each probe is recorded and saved into memory using a GUI controller.

Figure 8:
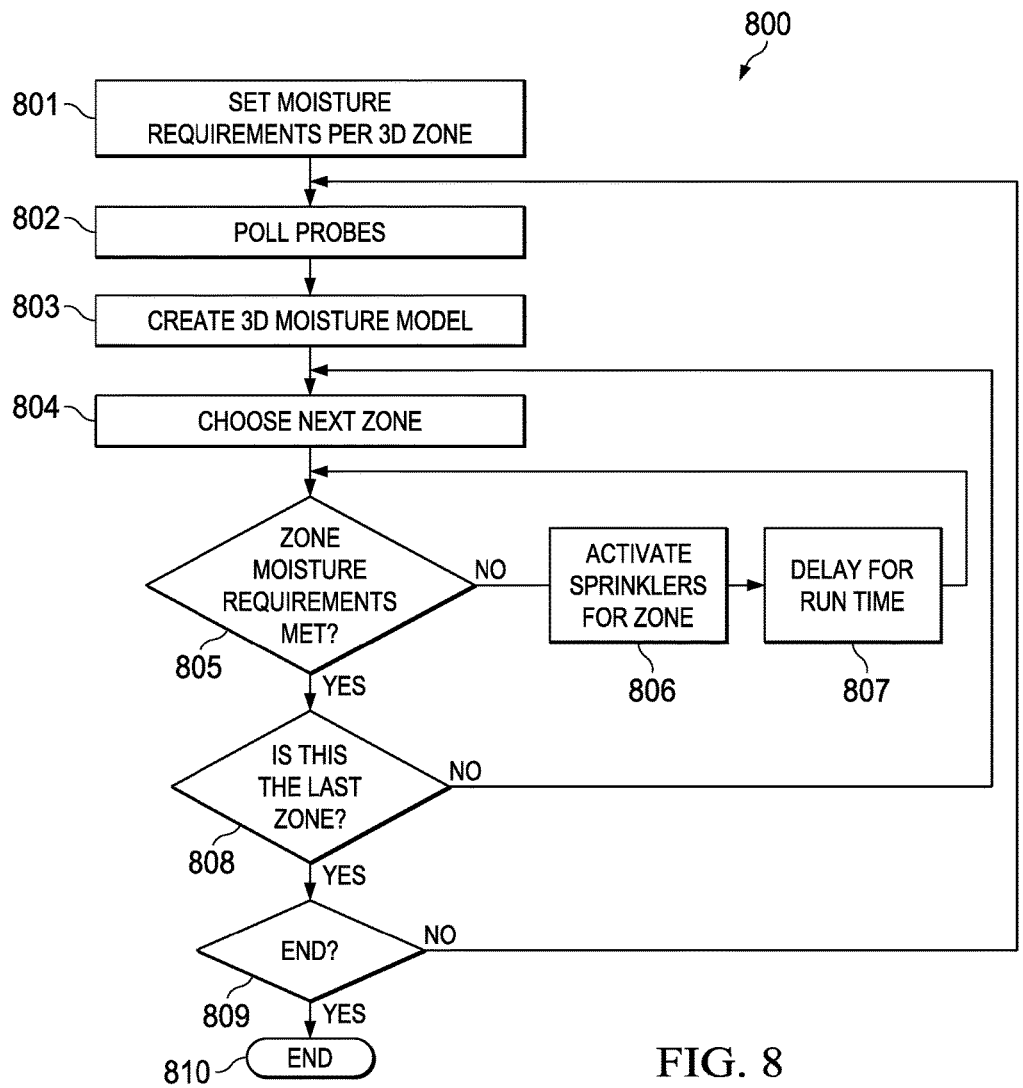
FIG. 8 is a flowchart of a runtime process of a preferred embodiment.

Referring to FIG. 8, control process 800 will be described. At step 801, the GUI controller is used to enter and create a set of moisture requirements for each three-dimensional zone. In a preferred embodiment, the three-dimensional zone corresponds to a grid pattern which matches the probe arrangement as shown in FIG. 2. In one embodiment, the set of moisture requirements are determined by the type of foliage planted in the zone. In one embodiment, a set of moisture requirements is downloaded and saved into memory in the form of a look-up table.

In one embodiment, a set of water restrictions is downloaded and saved into memory. The set of water restrictions determine when a property owner can water their lawn. For example, the set water restrictions limit watering to Tuesdays and Thursdays and not between the hours of 10 am to 6 pm.

In one embodiment, a set of weather conditions is downloaded and saved into memory.

At step 802, the probe controller polls the probes for measurements. At step 803, a 3-D moisture model is generated from the probe measurement data. At step 804, a predetermined zone or set of zones is selected. At step 805, the zone moisture requirements for the predetermined zone or set of zones are compared to the moisture present as indicated from the moisture model. If the zone moisture requirements are not met, then at step 806, the sprinkler controller is activated by a set of sprinkler commands generated by the computer for that particular zone, or for the set of zones.

In one embodiment, the set of sprinkler commands includes a watering schedule based on the set of watering restrictions.

In one embodiment, the set of sprinkler commands includes a water schedule based on the set of weather conditions. For example, the sprinkler commands will not activate the sprinklers if it is raining or if rain is expected within a predetermined time. In another example, the sprinkler commands will not activate if the temperature is below 32° Fahrenheit or the temperature will be below 32° Fahrenheit within a predetermined period of time.

In one embodiment, the set of sprinkler commands includes a watering schedule based on the set of watering restrictions and the set of weather conditions.

At step 807, the sprinkler controller delays for a predetermined nm time to allow the sprinklers to run. After the predetermined run time, the method returns to step 805. If at step 805, the zone moisture requirements are met, then the method moves to step 808. At step 808, the method determines if the last zone has been checked. If not, the method moves to step 804, where it advances to the next zone. If the last zone has been checked, then method 800 proceeds to step 809. At step 809, whether an end command has been received is determined. If an end command has not been received, then method 800 returns to step 802 and acquires additional probe data. If an end command has been received, then method 800 ends at step 810.

Figure 9:
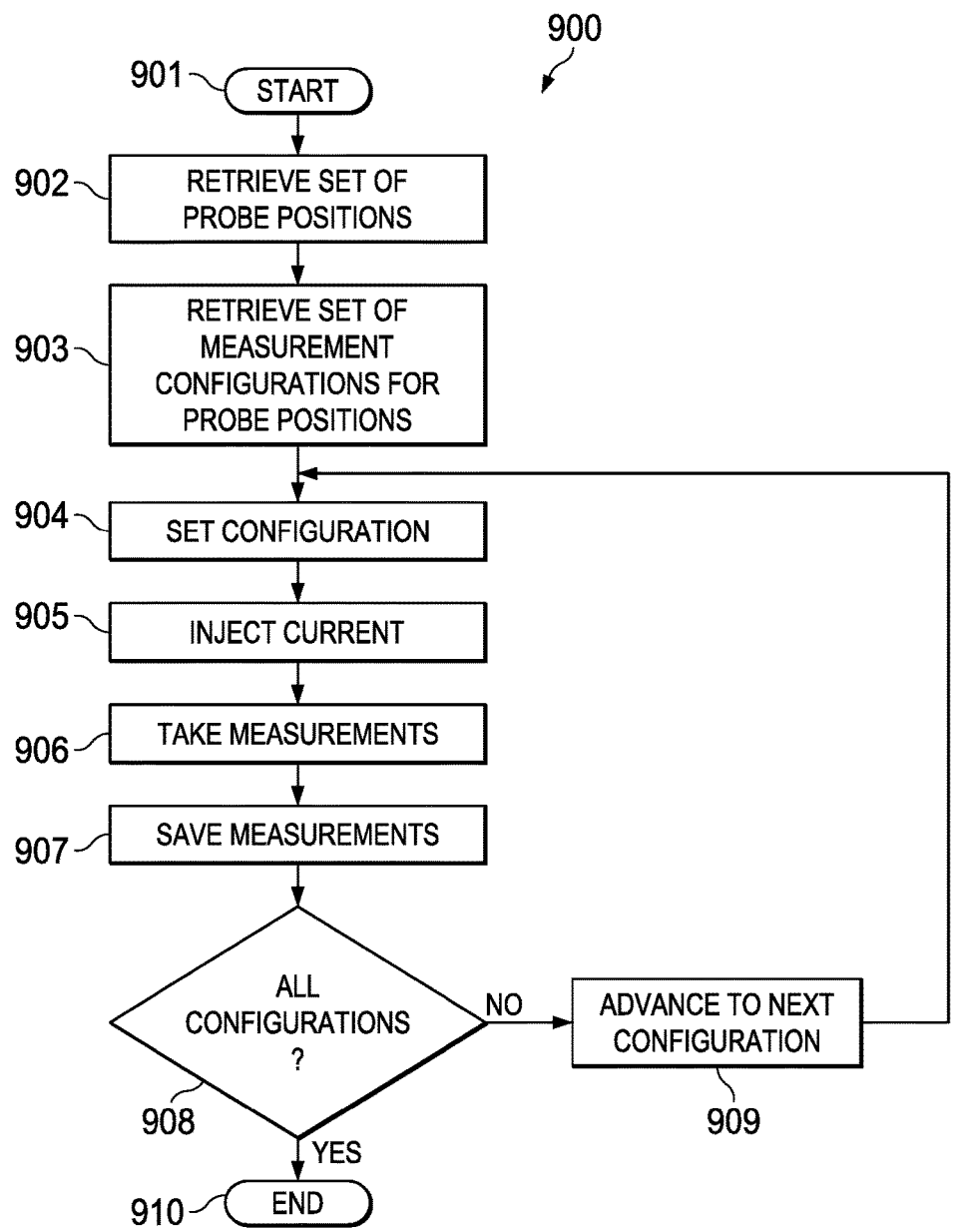
FIG. 9 is a flowchart of a method for polling a set of probes of preferred embodiment.

Referring to FIG. 9, step 802 will be further described as method 900 for polling the set of probes. Method 900 begins at step 901. At step 902, a set of probe positions is retrieved from memory. At step 903, a set of measurement configurations for the set of probes is retrieved. In a preferred embodiment, the set of measurement configurations is a set of instructions for injecting current to a subset of probes to inject current and to measure voltages, as previously described.

At step 904, a measurement configuration of the set of measurements is configuration is set. In this step, a probe controller configures a set of switches to connect to a reference probe and a set of measurement probes. At step 905, a current is injected into the ground through the set of probes. At step 906, a set of measurements is made from the set of probes. In this step, a set of voltages is measured. At step 907, the set of measurements is saved. At step 908, a determination of whether all configurations have been completed is made. If all configurations have not been completed, then method 900 proceeds to step 909. At step 909, method 900 advances to the next configuration in the set of configurations. If all configurations have been completed, then method 900 ends at step 910.

Figure 10:
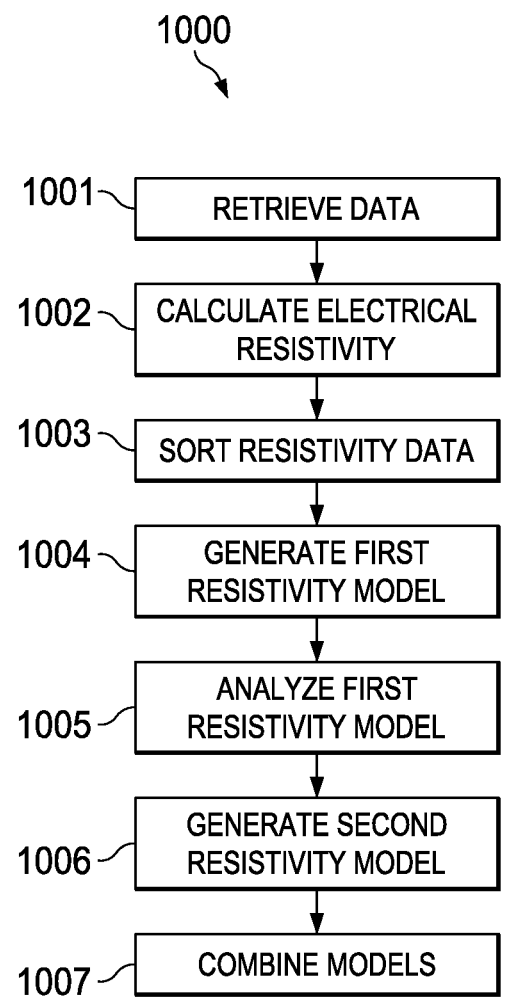
FIG. 10 is a flowchart of a method for creating a three-dimensional moisture map of a preferred embodiment.

Referring to FIG. 10, step 803 will be further described as method 1000 for generating a three-dimensional resistivity model. At step 1001, a set of measurement data is retrieved from memory. The set of measurement data includes a set of measured voltages and measured currents for each of a set of probe arrays, as previously described. At step 1002, a set of electrical resistivity calculations is calculated from the measured voltages and currents according to the following equation:

$$\rho_{nm} = K \frac{V_{nm}}{I} \qquad \text{Eq. 1}$$

where $\rho_{nm}$ is the current density between the probes at positions in and m, K is a probe geometric constant, $V_{nm}$ is the electric potential difference between two probes, a probe at position n and a probe at position, and I is the injected current which corresponds to the measured HV current. In this step, a set of virtual resistivity locations is calculated based on the known locations of the current probes and the voltage probes.

At step 1003, the set of resistivity calculations and the set of virtual resistivity locations are sorted into a number of discrete sets, each of which includes a set of spatial coordinates and a set of resistivity values at each set of spatial coordinates.

In a preferred embodiment, SWIFTCNV software from SAGA Geophysics, Inc. is used to perform step 1003. Other suitable software programs known in the art may be employed.

At step 1004, a least squares data inversion analysis on each of the discrete sets is performed to create a first electrical resistivity model that corresponds to each of the set of probe arrays, thereby creating a set of first electrical resistivity models. Each first electrical resistivity model minimizes the error of the measurement data.

In a preferred embodiment, RES2DLINV software from SAGA Geophysics, Inc. is employed. Any suitable software that performs least squares inversion and produces a two-dimensional graphical output may be employed.

At step 1005, a spatial data analysis is performed on each first electrical resistivity model using geostatistical methods known in the art, such as kriging. Other geostatistical methods known in the art may be employed. At step 1006, a set of second electrical resistivity model is generated that minimizes the error of the spatial variability of the set of first electrical resistivity models. In a preferred embodiment, SURFER software available from Golden Software, Inc. is employed. Any geostatistical analysis program known in the art may be used.

At step 1007, each second electrical resistivity model is combined to generate the three-dimensional resistivity model. In a preferred embodiment, each second electrical resistivity model corresponds to an array of probes. In a preferred embodiment, regression analysis is employed to "connect" the two-dimensional models to generate the three-dimensional model. The three-dimensional model corresponds to a grid.

In a preferred embodiment, SURFER software available from Golden Software, Inc. is employed. Any geostatistical analysis program known in the art may be used.

Figure 11:
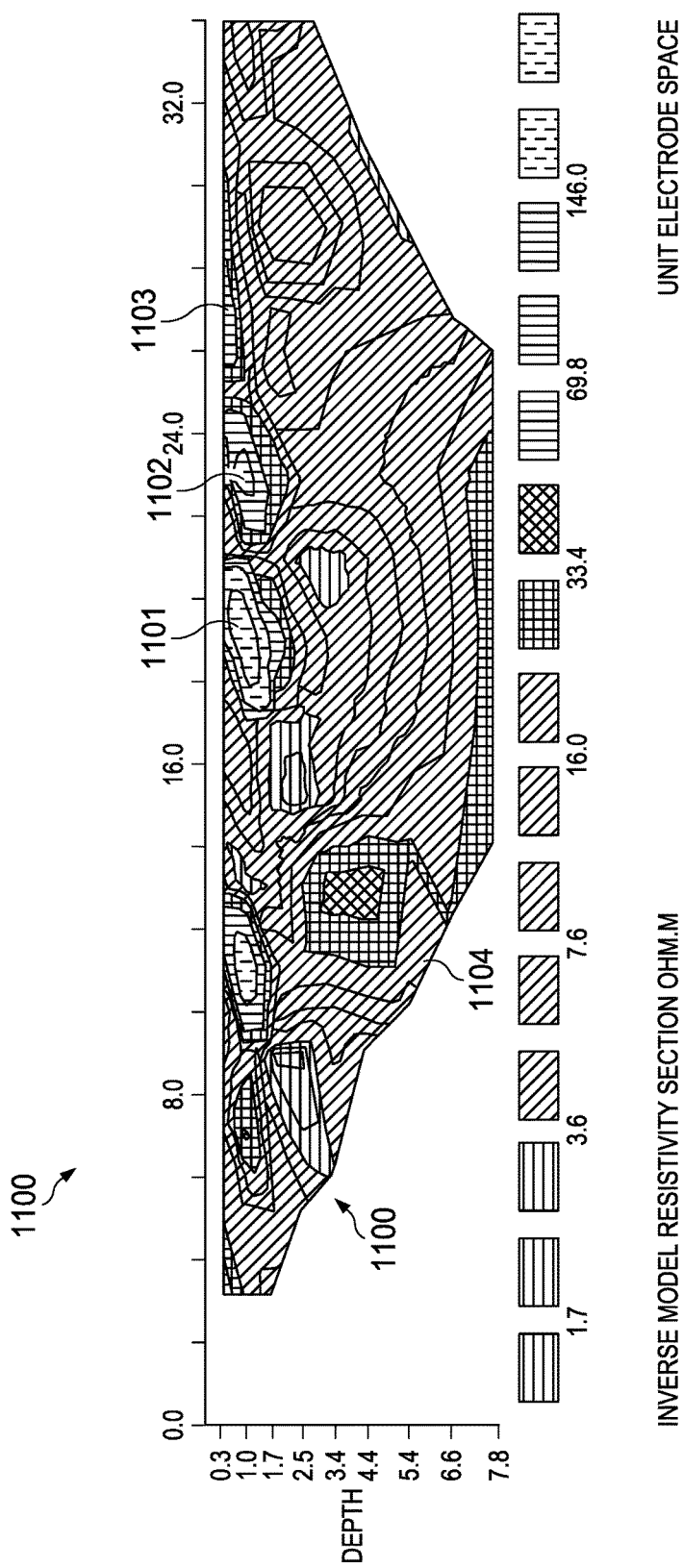
FIG. 11 is a resistivity map of a preferred embodiment.

Referring to FIG. 11, model 1100 is an example of a two-dimensional graphical output of the least squares data inversion analysis of step 1004. Model 1100 include sill-defined voids 1101, 1102, and 1103 and subsurface features such as sandbar 1104.

Figure 12:
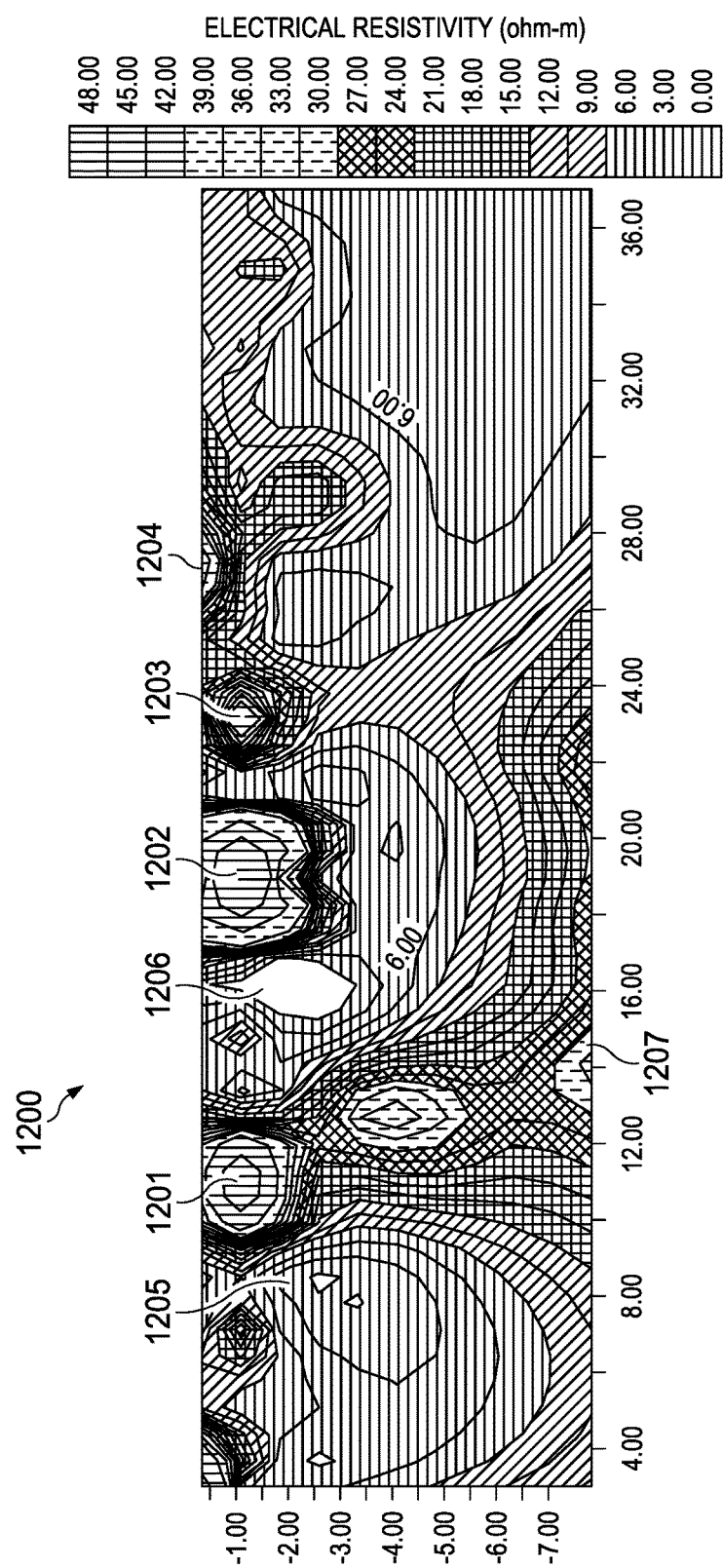
FIG. 12 is a resistivity map of a preferred embodiment.

Referring to FIG. 12, model 1200 is an example of a two-dimensional graphical representation of location and resistivity. Model 1200 is an example of a two-dimensional graphical output of the kriging analysis. As can be seen model 1200 shows with much greater clarity than model 1100, voids 1201, 1202, 1203, and 1204, ground water 1205, saturated soil 1206, and sandbar deposit 1207.

Figure 13:
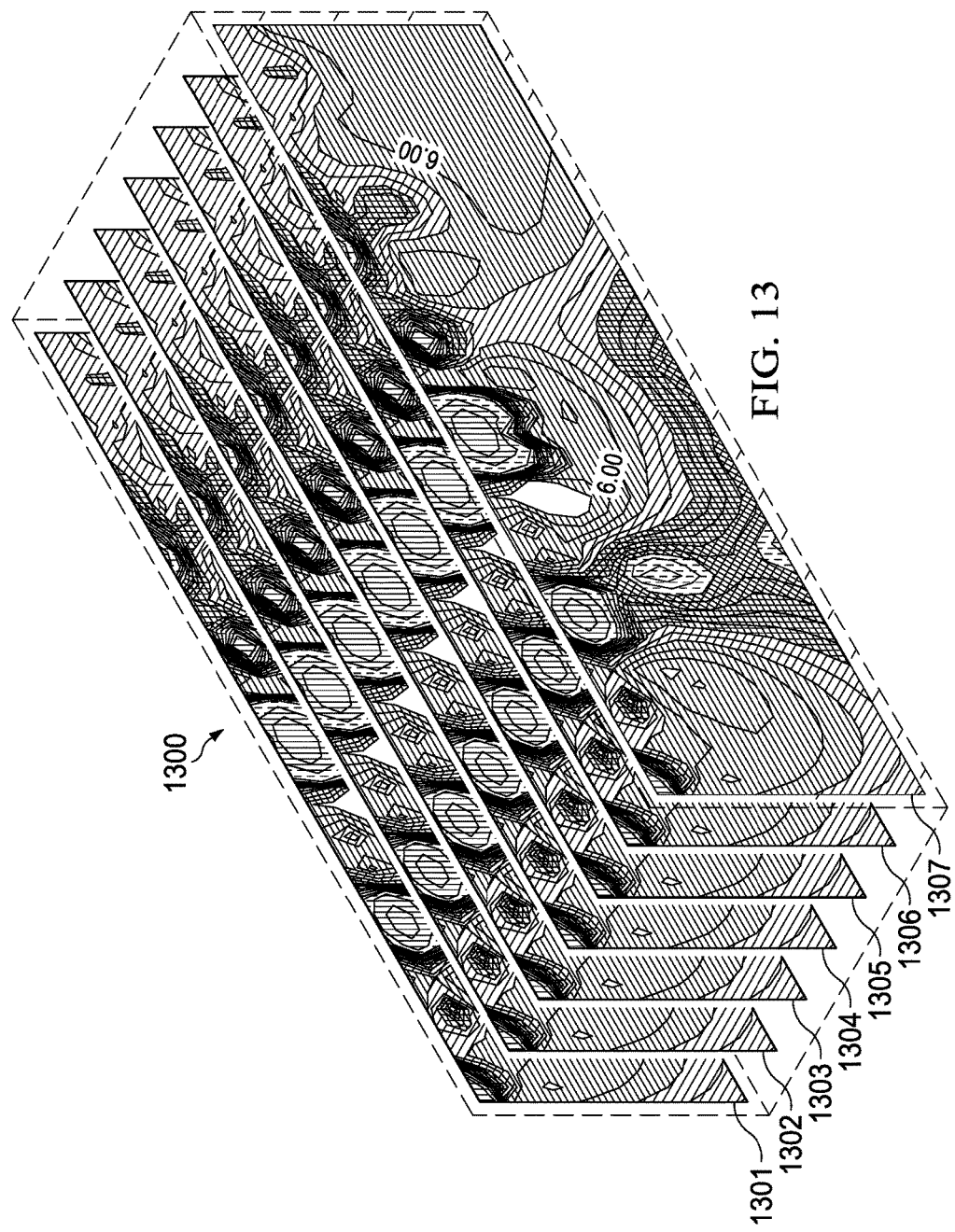
FIG. 13 is a three-dimensional resistivity map of a preferred embodiment.

Referring to FIG. 13, three-dimensional model 1300 includes two-dimensional models 1301, 1302, 1303, 1304, 1305, 1306, and 1307. In a preferred embodiment, each of two-dimensional models 1301, 1302, 1303, 1304, 1305, 1306, and 1307 corresponds to an array of probes. In a preferred embodiment, regression analysis is employed to "connect" the two-dimensional models to generate the three-dimensional model. The three-dimensional model corresponds to a grid.

It will be appreciated by those skilled in the art that the described embodiments disclose significantly more than an abstract idea including technical advancements in the field of data processing and a transformation of data which is directly related to real world objects and situations in that the disclosed embodiments enable a computer to operate more efficiently, enable a sprinkler system to operate more efficiently, and improve the efficient use of water. Specifically, the disclosed embodiments at least determine soil moisture levels in a more detailed way than systems and methods of the prior art and determine specific watering needs based on the detailed moisture levels, thereby leading to more efficient use of water and more efficient operation of a sprinkler system.

It will be appreciated by those skilled in the art that modifications can be made to the embodiments disclosed and remain within the inventive concept. Therefore, this invention is not limited to the specific embodiments disclosed, but is intended to cover changes within the scope and spirit of the claims.

The invention claimed is:

1. A system for moisture control comprising:
   a computer;
   a set of sprinkler controllers connected to the computer, each sprinkler controller controlling at least one sprinkler;
   a probe controller connected to the computer;
   a set of probes connected to the probe controller, each probe associated with a probe location, and comprising at least one reference probe;
   the probe controller programmed to measure a set of probe data by measuring voltages between the reference probe and each of a plurality of other probes and corresponding currents between pairs of the plurality of other probes;

the computer programmed to:
receive a three-dimensional set of moisture requirements including a set of surface zones associated with a set of depths below a surface related to types of foliage stored in a look-up table, each type of foliage associated with a watering depth;
receive the set of probe data;
calculate a set of resistivity data from the set of probe data, the probe locations, and a probe geometric constant;
sort the set of resistivity data to create a set of sorted resistivity data;
generate a set of first resistivity models from the set of sorted resistivity data;
generate a set of second resistivity models from the set of first resistivity models;
combine the set of second resistivity models to generate the three-dimensional resistivity model;
compare the three-dimensional resistivity model to the three-dimensional set of moisture requirements;
generate a set of sprinkler commands based on the comparison; and,
send the set of sprinkler commands to the set of sprinkler controllers activating the corresponding at least one sprinkler.

2. The system of claim 1, wherein:
the reference probe is switchably connected to the probe controller;
wherein a set of measurement probes is switchably connected to the probe controller; and,
wherein the probe controller is further programmed to:
implement a probe configuration for the reference probe and the set of measurement probes;
inject a current based on the probe configuration; and,
measure a voltage based on probe configuration.

3. The system of claim 1, further comprising:
a set of sprinklers, including the at least one sprinkler, connected to the set of sprinkler controllers; and wherein,
a subset of the set of surface zones is associated with a subset of the set of sprinklers; and,
each of the sprinklers in the subset of sprinklers is controlled by the set of sprinkler commands.

4. The system of claim 1, wherein the set of sprinkler commands further comprises a watering schedule based on one of a set of watering restrictions and a set of weather conditions.

* * * * *